United States Patent [19]

Auron et al.

[11] Patent Number: 4,762,914
[45] Date of Patent: Aug. 9, 1988

[54] TRUNCATED PROTEIN OF INTERLEUKIN-1

[76] Inventors: Philip E. Auron, 119 Wilson Dr., Framingham, Mass. 01701; Andrew C. Webb, 6 Lovewell Rd., Wellesley, Mass. 02181; Lee Gehrke, 11 Blueberry Cir., Framingham, Mass. 01701; Charles A. Dinarello, 133 Mt. Vernon St., Boston, Mass. 02108; Lanny J. Rosenwasser, 58 Sherburn Cir., Weston, Mass. 02193; Alexander Rich, 2 Walnut Ave., Cambridge, Mass. 02140; Sheldon M. Wolff, 12 Lowell Rd., Wellesley, Mass. 02181

[21] Appl. No.: 700,374

[22] Filed: Feb. 11, 1985

Related U.S. Application Data

[63] Continuation-in-part of Ser. No. 611,699, May 18, 1984, abandoned.

[51] Int. Cl.$^4$ ............................................. C07K 13/00
[52] U.S. Cl. .................................... 530/351; 530/350; 530/300; 530/324; 530/806; 435/68; 435/70; 935/47; 935/60; 935/109
[58] Field of Search .................. 530/351, 350; 435/68, 435/70; 935/47, 60, 109

[56] References Cited

FOREIGN PATENT DOCUMENTS 0101363 2/1984 European Pat. Off. .
8500830 2/1985 France .
0149386 8/1985 Japan .

OTHER PUBLICATIONS

Mizil, *Immunol. Rev.* 1982, vol. 36, pp. 51–73.
Mizel et al., *J. Immunol.*, pp. 834–837, 1981, vol. 126(3).
Lachman, *Fed. Proc.* 42, 1983, pp. 2639–2645.
Lachman et al., *J. Supramolecular Structure*, 13(4), 1980, pp. 109–118.
Prestidge et al., *J. Cellular Biochem.* 26, 1984, pp. 65–73.
Wood et al., *Immunol.* 50, 1983, pp. 637–644.
Oppenheim et al., *T Lymphocyte Today* 1983, pp. 89–95.
Windle et al., *J. Immunol.*, 132, 1984, pp. 1317–1322.
*Nature*, vol. 312, 1984, pp. 458–462, Lomedico et al.
Dinarello, C. A. (1984), "Interleukin-1 and the Pathogenesis of the Acute-14 Phase Response", New Eng. Journ. Med. 311:1413–1418.
Auron, P. E. et al. (1984) "Nucleotide Sequence of Human Monocyte Interleukin-1 Precursor cDNA", Proc. Natl. Acad. Sci. USA 81:7907–7911.

*Primary Examiner*—J. R. Brown
*Assistant Examiner*—Garnette D. Draper

[57] ABSTRACT

The subject invention concerns truncated human IL-1 cDNA sequences which encode biologically-active novel human IL-1 proteins. These truncated human IL-1 cDNA sequences can be obtained by genetic engineering procedures using a clone of human IL-1 cDNA, having the accession number NRRL B-15770, as a starting material. The truncated human IL-1 cDNA sequences of the subject invention are contained in specified plasmids whose constructions are described in detail. Biologically-active human IL-1 proteins are useful to induce the production of IL-2 by activated T-cells. They also act on B-cells and NK-cells.

3 Claims, No Drawings

TRUNCATED PROTEIN OF INTERLEUKIN-1

CROSS REFERENCE TO A RELATED APPLICATION

This is a continuation-in-part of our copending application Ser. No. 611,669, filed on May 18, 1984 now abandoned.

BACKGROUND OF THE INVENTION

Interleukin 1 (IL-1) is a protein produced by activated mononuclear phagocytes and performs a broad range of functions in host defense and immunoregulation (Dinarello, C. A. [1984] New England J. Med. 311, 1413–1418). Recently it has been demonstrated that Il-1 is first synthesized as a precursor molecule of about 270 amino acids in length (approximately 30,000 molecular weight) which is proteolytically processed into a smaller molecule (approximately 18,000 molecular weight) which possesses full biological activity (Auron, P. E., Webb, A. C., Rosenwasser, L. J., Mucci, S. F., Rich, A., Wolff, S. M., and Dinarello, C. A. [1984] Proc. Natl. Acad. Sci. USA 81). The sequence for human IL-1 is shown in Chart A.

BRIEF SUMMARY OF THE INVENTION

The subject invention concerns truncated human IL-1 cDNA sequences which encode biologically-active human IL-1 proteins. These truncated cDNA sequences, and novel biologically-active human IL-1 proteins obtained therefrom, can be obtained by genetic engineering procedures using a clone containing the entire human IL-1 cDNA sequence as starting material. Specifically, with reference to Chart A, the nucleotide sequence located between residues 534 and 893 encode biologically-active IL-1 proteins. Within this range are two regions which encode biologically-active IL-1 proteins; i.e., (1) the nucleotide sequence located between residues 534 and 710, and (2) the nucleotide sequence located between residues 711 and 893.

DETAILED DESCRIPTION OF THE INVENTION

The subject invention, advantageously, provides novel biologically-active human IL-1 proteins through use of novel truncated human IL-1 cDNA sequences. As disclosed above, the entire human IL-1 cDNA sequence is shown in Chart A. This sequence is the starting material for the preparation of the novel clones of the subject invention, as disclosed hereinafter in the Examples.

Clone (plasmid)pcD-415, which contains the cDNA for human monocyte IL-1, was deposited in an *E. coli* HB101 host in the permanent collection of the Northern Regional Research Laboratory, U.S. Department of Agriculture, Peoria, Ill., USA, on Apr. 27, 1984. The culture was assigned the accession number NRRL B-15770 by the repository. This deposit is available to the public upon the grant of a patent disclosing it. The deposit is also available as required by foreign patent laws in countries when counterparts of the subject application, or its progeny, are filed. However, it should be understood that the availability of a deposit does not constitute a license to practice the subject invention in derogation of patent rights granted by governmental action.

Recombinant plasmid pcD-415 can be isolated from its *E. coli* HB101 host by well-known procedures, e.g., using cleared lysate-isopycnic density gradient procedures, and the like.

Unlimited amounts of nucleic acid comprising nucleotide sequences coding for truncated human IL-1 can be made by the cloned human IL-1 cDNA of the subject invention. Further, the IL-1 proteins produced by the cloned cDNA of the subject invention can be used to induce the production of IL-2 by activating T-cells-IL-2 stimulates the T-cells to proliferate. As reported in *Science*, 221, 1362–1364, "Researchers from NIAID and the Food and Drug Administration (FDA), using a test tube assay, have recently found that interleukin-2 improved the function of T-cells from six AIDS patients" (p. 1362). In summary, the novel biologically-active human IL-1 proteins obtained via the cloned truncated human IL-1 cDNA sequences of the subject invention can be used in the same manner as native human IL-1.

The following examples are illustrative of the process and products of the subject invention but are not to be construed as limiting. All percentages are by weight and all solvent mixture proportions are by volume unless otherwise noted.

EXAMPLE 1

Construction of a Plasmid Containing Truncated Human IL-1 cCNA That Codes for Proteins Corresponding to the DNA Sequences Located Between Nucleotide Positions 87 Through 677, and Positions 1355 Through 1396 Shown in Chart A The IL-1 cDNA sequence (Chart A) contains three unique restriction endonuclease digestion sites that can be used to construct plasmids containing specific deletions aimed at isolating essential domains of IL-1. Proceeding 5' to 3' in the directional sense of protein coding by the cDNA, these three sites are located respectively named and positioned as follows: Hind III (pos. 483); Pvu II (pos. 678); and Xmn I (pos. 1355) (Note: all restriction endonuclease sites presented here are referenced to the location of the first nucleotide on the 3' side of scission as read along the protein coding "sense" strand of the cDNA). In addition a unique Pst I restriction site located upstream from the cDNA sequence (pos. −16) can also be used.

The first plasmid construction deletes all IL-1 cDNA nucleotide sequence between the Pvu II and Xmn I sites, described above, and is as follows: Plasmid pL1, as described by H. Okayama and P. Berg (1983) Molec. Cell. Biol. 3:280–289, and which can be purchased from Pharmacia (Piscataway, NJ), is digested completely with Xmn I and Hind III restriction endonucleases. Three products which result can be resolved by agarose gel electrophoresis.

These products are approximately 518, 782, and 1544 base pairs in length. The 518 base pair fragment is isolated from the agarose gel using standard techniques. Another plasmid, e.g., pUC-8 (Messing, J. and Vieira, J. [1982] Gene 19:269–276), which can be purchased from Pharmacia, is used as source of a DNA fragment which can be used as a linker segment to attach the Pst I restriction site located at one end of the 518 base pair fragment to a Hind III site which will be described below. pUC-8 contains a polycloning site with adjacent Pst I and Hind III sites and can be substituted for by other similar DNAs such as pUC-9 or M13mp8 or M13mp9 double stranded replicative forms. These DNAs can be purchased from Pharmacia. The pUC-8 plasmid is digested with Pst I and mixed with the 518 base pair fragment derived from pL1. The two fragments are ligated by T4 DNA ligase under conditions of excess pUC-8. Two products which result represent two different ligated orientations of the 518 fragment with respect to the linearized pUC-8. The two different orientations cannot easily be isolated from each other since each possesses the same molecular size (approximately 3660 base pairs). Isolation is accomplished by first digesting the 3660 base pair DNA mixture with Hind III endonuclease which causes the original mixture to be fragmented into 4 products of approximately 3650, 3140, 528, and 10 base pairs in length. These products can readily be resolved by standard agarose gel electrophoresis and the 528 base pair, pL1-derived, fragment (which now possess Hind III cohesive ends) is isolated.

The original human IL-1 cDNA plasmid (pcD-415), contained in the *E. coli* HB101 host, is isolated using standard plasmid preparation procedures. This plasmid is digested with both Pvu II and Xmn I restriction endonucleases to yield three products which are resolvable by agarose gel electrophoresis (approximate sizes are 675, 1633, and 2379 base pairs). The 1633 and 2379 base pair fragments are isolated from the gel and ligated in the presence of T4 DNA ligase to the pL1-derived, 528 base-pair fragment, described above. Two different plasmid constructs result, one of which has the proper orientation for the DNA fragments. The correct construct can readily be isolated by taking advantage of the fact that the ampicillin resistance gene contained within the pcD-415 plasmid will be properly reassembled only in the plasmid construction containing the desired IL-1 cDNA fragment orientation. Therefore *E. coli* HB101 cells transformed with the mixture containing both plasmids will only yield viable *E. coli* cells containing the proper construct when the cells are grown in the presence of ampicillin. From these cells the final construct (which is referred to as pcD-415ΔPvu/Xmn) can be isolated using standard plasmid isolation procedures. This plasmid contains truncated human IL-1 cDNA that codes for a protein corresponding to the DNA sequence located between nucleotide positions 87 through 677 and positions 1355 through 1396 shown in Chart A.

EXAMPLE 2

Construction of a Plasmid Containing Truncated Human IL-1 cDNA that Codes for a Protein Corresponding to the DNA Sequence Located Between Nucleotide Positions 492 Through 893 Shown in Chart A This plasmid is constructed such that all the cDNA sequence between the upstream Pst I site and the Hind III site contained within the human IL-1 sequence is deleted. The starting material is plasmid pcD-415. Plasmid pcD-415 is digested with Hind III endonuclease and the two products (approximately 1016 and 3676 base pairs) resolved by agarose gel electrophoresis. The 3676 base pair fragment is isolated from the gel and mixed with the pL1-derived, 528 base pair (Hind III cohesive-ended) fragment prepared for use in constructing pcD-415ΔPvu/Xmn in Example 1. Ligation of these DNAs by T4 ligase results in two different plasmid products which can be purified and distinguished by transformation of *E. coli* HB101 cells and restriction mapping of the isolated plasmids. A Pvu II and Pst I double digestion permits clear identification of the product. The final product with the required deletion is referred to as pcD-415ΔPst/Hin. This plasmid contains a truncated human IL-1 cDNA that codes for a protein corresponding to the DNA sequence located between nucleotide positions 492 through 893 shown in Chart A.

EXAMPLE 3

Construction of a Plasmid Containing Truncated Human IL-1 cDNA that Codes for Proteins Corresponding to the DNA Sequence Located Between Nucleotide Positions 492 Through 677 and Positions 1355 Through 1396 Shown in Chart A This construction is a combination of both deletions described above located within a single plasmid. The pcD-415ΔPst/Hin plasmid, described above, is digested with Pvu II and Xmn I to yield three agarose gel resolvable products (approximately 675, 1150, and 2379 base pairs). The 1150 and 2379 base pair fragments are isolated and ligated to yield two possible products which can be resolved in a fashion analogous to that described in Example 1 by selection of transformed *E. coli* HB101 in the presence of ampicillin. The final product with the required deletions is referred to as pcD-415ΔPst/HinΔPvu/Xho.

This plasmid contains a truncated human IL-1 cDNA that codes for proteins corresponding to the DNA sequence located between nucleotide positions 492 through 677 and positions 1355 through 1396 shown in Chart A.

The cDNA transcript can be obtained from the clones in essentially pure form by standard art methods. For example, the cDNA transcript can be clipped from a plasmid by a BamHI-Pst I double-digestion (Okayama, H. and Berg, P. [1983] Molec. Cell. Biol. 3:280-289) and isolated by standard procedures. The essentially pure cDNA thus obtained can be used for subcloning into a different transfer vector.

As is well known in the art, the amino acid sequence of a protein, e.g., the IL-1 proteins of the invention, is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
|---|---|---|---|
| Leucine (Leu) | XTY | Glutamine (Gln) | CAJ |
| Isoleucine (Ile) | ATH | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Try) | TGG |
| Alanine (Ala) | GCL | Arginine (Arg) | WGZ |
| Tyrosine (Tyr) | TAK | Glycine (Gly) | GGL |
| Termination Signal | TAJ | | |
| Termination signal | TGA | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A=adenine

G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T
J = A or G
K = T or C
L = A, T, C or G
M = A, C or T The above shows that the novel amino acid sequences of the human IL-1 proteins of the subject invention can be prepared by nucleotide sequences other than those disclosed herein. Functionally equivalent nucleotide sequences encoding the novel amino acid sequences of these human IL-1 proteins, or fragments thereof having IL-1 activity, can be prepared by known synthetic procedures. Accordingly, the subject invention includes such functionally equivalent nucleotide sequences.

Thus the scope of the subject invention includes not only the specific nucleotide sequences depicted herein, but also all equivalent nucleotide sequences coding for molecules with substantially the same human IL-1 biological activity. The term "equivalent" is being used in its ordinary patent usage here as denoting a nucleotide sequence which performs substantially as the nucleotide sequence identified herein to produce molecules with substantially the same human IL-1 biological activity in essentially the same kind of hosts. Within this definition are subfragments which have human IL-1 biological activity.

It is well within the skill of those in the genetic engineering art to use the nucleotide sequences encoding human IL-1 activity of the subject invention to produce human IL-1 proteins via microbial processes. Fusing the sequences into an expression vector and transforming or transfecting into hosts, either eukaryotic (yeast or mammalian cells) or prokaryotic (bacterial cells), are standard procedures used in producing other well-known proteins, e.g., insulin, interferons, human growth hormone, and the like. Similar procedures, or obvious modifications thereof, can be employed to prepare human IL-1 proteins by microbial means or mammalian tissue-culture technology in accord with the subject invention.

The nucleotide sequences obtained from IL-1 clone pCD-415 also can be prepared by a "gene machine" by procedures well known in the art. This is possible because of the disclosure of the nucleotide sequence. However, it is generally recognized in the art at this time that obtention of the desired nucleotide sequence from a clone, e.g., pCD-415, is the most expedient way to practice an invention such as disclosed and claimed herein.

The restriction enzymes disclosed can be purchased from Bethesda Research Laboratories, Gaithersburg, MD, or New England Biolabs, Beverly, MA. The enzymes are used according to the instructions provided by the supplier.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, e.g., *E. coli* cells, prepare plasmid DNA, electrophorese proteins, and sequence DNA.

CHART A

```
A C A A A A C C T T T T C G A G G C A A A A G G C A A A A A A
         10           20           30

G G C T G C T G G G A T T C T C T T C A G C C A A T C T
         40           50           60

MET  ALA
T C A A T G C T C A A G T G T C T G A A G C A G C C A T G G
         70           80           90

GLU  VAL  PRO  LYS  LEU  ALA  SER  GLU  MET  MET
C A G A A G T A C C T A A G C T C G C C A G T G A A A T G A
         100          110          120

ALA  TYR  TYR  SER  GLY  ASN  GLU  ASP  ASP  LEU
T G G C T T A T T A C A G T G G C A A T G A G G A T G A C T
         130          140          150

PHE  PHE  GLU  ALA  ASP  GLY  PRO  LYS  GLN  MET
T G T T C T T T G A A G C T G A T G G C C C T A A A C A G A
         160          170          180

LYS  CYS  SER  PHE  GLN  ASP  LEU  ASP  LEU  CYS
T G A A G T G C T C C T T C C A G G A C C T G G A C C T C T
         190          200          210

PRO  LEU  ASP  GLY  GLY  ILE  GLN  LEU  ARG  ILE
G C C C T C T G G A T G G C G G C A T C C A G C T A C G A A
         220          230          240
```

-continued

CHART A

```
    SER  ASP  HIS  HIS  TYR  SER  LYS  GLY  PHE  ARG
   T C T C C G A C C A C C A C T A C A G C A A G G G C T T C A
              250            260            270

GLN  ALA  ALA  SER  VAL  VAL  VAL  ALA  MET  ASP
   G G C A G G C C G C G T C A G T T G T T G T G G C C A T G G
              280            290            300

LYS  LEU  ARG  LYS  MET  LEU  VAL  PRO  CYS  PRO
   A C A A G C T G A G G A A G A T G C T G G T T C C C T G C C
              310            320            330

GLN  THR  PHE  GLN  GLU  ASN  ASP  LEU  SER  THR
   C A C A G A C C T T C C A G G A G A A T G A C C T G A G C A
              340            350            360

PHE  PHE  PRO  PHE  ILE  PHE  GLU  GLU  GLU  PRO
   C C T T C T T T C C C T T C A T C T T T G A A G A A G A A C
              370            380            390

ILE  PHE  PHE  ASP  THR  TRP  ASP  ASN  GLU  ALA
   C T A T C T T C T T C G A C A C A T G G G A T A A C G A G G
              400            410            420

TYR  VAL  HIS  ASP  ALA  PRO  VAL  ARG  SER  LEU
   C T T A T G T G C A C G A T G C A C C T G T A C G A T C A C
              430            440            450

ASN  CYS  THR  LEU  ARG  ASP  SER  GLN  GLN  LYS
   T G A A C T G C A C G C T C C G G G A C T C A C A G C A A A
              460            470            480

SER  LEU  VAL  MET  SER  GLY  PRO  TYR  GLU  LEU
   A A A G C T T G G T G A T G T C T G G T C C A T A T G A A C
              490            500            510

LYS  ALA  LEU  HIS  LEU  GLN  GLY  GLN  ASP  MET
   T G A A A G C T C T C C A C C T C C A G G G A C A G G A T A
              520            530            540

GLU  GLN  GLN  VAL  VAL  PHE  SER  MET  SER  PHE
   T G G A G C A A C A A G T G G T G T T C T C C A T G T C C T
              550            560            570

VAL  GLN  GLY  GLU  GLU  SER  ASN  ASP  LYS  ILE
   T T G T A C A A G G A G A A G A A A G T A A T G A C A A A A
              580            590            600

PRO  VAL  ALA  LEU  GLY  LEU  LYS  GLU  LYS  ASN
   T A C C T G T G G C C T T G G G C C T C A A G G A A A A G A
              610            620            630

LEU  TYR  LEU  SER  CYS  VAL  LEU  LYS  ASP  ASP
   A T C T G T A C C T G T C C T G C G T G T T G A A A G A T G
              640            650            660

LYS  PRO  THR  LEU  GLN  LEU  GLU  SER  VAL  ASP
   A T A A G C C C A C T C T A C A G C T G G A G A G T G T A G
              670            680            690

PRO  LYS  ASN  TYR  PRO  LYS  LYS  LYS  MET  GLU
   A T C C C A A A A A T T A C C C A A A G A A G A A G A T G G
              700            710            720

LYS  ARG  PHE  VAL  PHE  ASN  LYS  ILE  GLU  ILE
   A A A A G C G A T T T G T C T T C A A C A A G A T A G A A A
              730            740            750

ASN  ASN  LYS  LEU  GLU  PHE  GLU  SER  ALA  GLN
   T C A A T A A C A A G C T G G A A T T T G A G T C T G C C C
              760            770            780
```

-continued

CHART A

```
      PHE PRO ASN TRP TYR ILE SER THR SER GLN
    A G T T C C C C A A C T G G T A C A T C A G C A C C T C T C
          790               800               810

ALA GLU ASN MET PRO VAL PHE LEU GLY   GLY
    A A G C A G A A A A C A T G C C C G T C T T C C T G G G A G
          820               830               840

THR LYS GLY GLY GLN ASP  ILE THR ASP  PHE
    G G A C C A A A G G C G G C C A G G A T A T A A C T G A C T
          850               860               870

THR MET GLN PHE VAL SER SER  ***
    T C A C C A T G C A A T T T G T G T C T T C C T A A A G A G
          880               890               900

A G C T G T A C C C A G A G A G T C C T G T G C T G A A T G
          910               920               930

T G G A C T C A A T C C C T A G G G C T G G C A G A A A G G
          940               950               960

G A A C A G A A A G G T T T T T G A G T A C G G C T A T A G
          970               980               990

C C T G G A C T T T C C T G T T G T C T A C A C C A A T G C
          1000              1010              1020

C C A A C T G C C T G C C T T A G G G T A G T G C T A A G A
          1030              1040              1050

G G A T C T C C T G T C C A T C A G C C A G G A C A G T C A
          1060              1070              1080

G C T C T C T C C T T T C A G G G C C A A T C C C A G C C C
          1090              1100              1110

T T T T G T T G A G C C A G G C C T C T C T C A C C T C T C
          1120              1130              1140

C T A C T C A C T T A A A G C C C G C C T G A C A G A A A C
          1150              1160              1170

C A G G C C A C A T T T T G G T T C T A A G A A A C C C T C
          1180              1190              1200

C T C T G T C A T T C G C T C C C A C A T T C T G A T G A G
          1210              1220              1230

C A A C C G C T T C C C T A T T T A T T T A T T T A T T T G
          1240              1250              1260

T T T G T T T G T T T T G A T T C A T T G G T C T A A T T T
          1270              1280              1290

A T T C A A A G G G G G C A A G A A G T A G C A G T G T C T
          1300              1310              1320

G T A A A A G A G C C T A G T T T T T A A T A G C T A T G G
          1330              1340              1350

A A T C A A T T C A A T T T G G A C T G G T G T G C T C T C
          1360              1370              1380

T T T A A A T C A A G T C C T T T A A T T A A G A C T G A A
          1390              1400              1410

A A T A T A T A A G C T C A G A T T A T T T A A A T G G G A
          1420              1430              1440

A T A T T T A T A A A T G A G C A A A T A T C A T A C T G T
          1450              1460              1470
```

CHART A -continued

```
TCAATGGTTCTCAAATAAACTTCACTAAAA
        1480         1490        1500
AAAAAAA
```

We claim:
1. A protein having the following amino acid sequence:

MET ALA GLU VAL PRO LYS LEU ALA SER GLU
MET MET ALA TYR TYR SER GLY ASN GLU ASP
ASP LEU PHE PHE GLU ALA ASP GLY PRO LYS
GLN MET LYS CYS SER PHE GLN ASP LEU ASP
LEU CYS PRO LEU ASP GLY GLY ILE GLN LEU
ARG ILE SER ASP HIS HIS TYR SER LYS GLY
PHE ARG GLN ALA ALA SER VA; VAL VAL ALA
MET ASP LYS LEU ARG LYS MET LEU VAL PRO
CYS PRO GLN THE PHE GLN GLU ASN ASP LEU
SER THR PHE PHE PRO PHE ILE PHE GLU GLU
GLU PRO ILE PHE PHE ASP THR TRP ASP ASN
GLU ALA TYR VAL HIS ASP ALA PRO VAL ARG
SER LEU ASN CYS THR LEU ARG ASP SER GLN
GLN LYS SER LEU VAL MET SER GLY PRO TYR
GLU LEU LYS ALA LEU HIS LEU GLN GLY GLN
ASP MET GLU GLN GLN VAL VAL PHE SER MET
SER PHE VAL GLN GLY GLU GLU SER ASN ASP
LYS ILE PRO VAL ALA LEU GLY LEU LYS GLU
LYS ASN LEU TYR LEU SER CYS VAL LEU LYS
ASP ASP LYS PRO THR LEU GLN ASN SER ILE
TRP THR GLY VAL LEU SER LEU ASN GLN VAL LEU.

2. A protein having the following amino acid sequence:

MET SER GLY PRO TYR GLU LEU LYS ALA LEU HIS LEU GLN GLY GLN
ASP MET GLU GLN GLN VAL VAL PHE SER MET SER PHE VAL GLN GLY
GLU GLU SER ASN ASP LYS ILE PRO VAL ALA LEU GLY LEU LYS GLU
LYS ASN LEU TYR LEU SER CYS VAL LEU LYS ASP ASP LYS PRO THR
LEU GLN LEU GLU SER VAL ASP PRO LYS ASN TYR PRO LYS LYS LYS
MET GLU LYS ARG PHE VAL PHE ASN LYS ILE GLU ILE ASN ASN LYS
LEU GLU PHE GLU SER ALA GLN PHE PRO ASN TRP TYR ILE SER THR
SER GLN ALA GLU ASN MET PRO VAL PHE LEU GLY GLY THR LYS GLY
GLY GLN ASP ILE THR ASP PHE THR MET GLN PHE VAL SER SER.

3. A protein having the following amino acid sequence:

MET SER GLY PRO TYR GLU LEU LYS ALA LEU HIS LEU GLN GLY GLN
ASP MET GLU GLN GLN VAL VAL PHE SER MET SER PHE VAL GLN GLY
GLU GLU SER ASN ASP LYS ILE PRO VAL ALA LEU GLY LEU LYS GLU
LYS ASN LEU TYR LEU SER CYS VAL LEU LYS ASP ASP LYS PRO THR
LEU GLN ASN SER ILE TRP THR GLY VAL LEU SER LEU ASN GLN VAL LEU.

* * * * *

UNITED STATES PATENT AND TRADEMARK OFFICE
CERTIFICATE OF CORRECTION

PATENT NO. : 4,762,914
DATED : August 9, 1988
INVENTOR(S) : Auron et al.

It is certified that error appears in the above-identified patent and that said Letters Patent is hereby corrected as shown below:

Title page: After names of inventors, insert --Assignees: New England Medical Center; Tufts College, both of Boston; Wellesley College, Wellesley; MIT, Cambridge, all of Mass.

After name of Examiner, insert --Attorney, firm, or agent: Roman Saliwanchik; David R. Saliwanchik--.

Column 6: Chart A, line 1: "ACAAAACCTTT" should read
                                      10
--ACAAACCTTT--.
       10

Chart A, line 2: "GGCTGCTG" should read
                                 40
--GGCTGCTCTG--.
       40

Column 11: line 17: 7th codon "VA;" should read --VAL--.

Signed and Sealed this

Nineteenth Day of September, 1989

Attest:

DONALD J. QUIGG

Attesting Officer                Commissioner of Patents and Trademarks